(12) United States Patent
Seaver et al.

(10) Patent No.: US 9,393,388 B2
(45) Date of Patent: Jul. 19, 2016

(54) SYSTEMS AND METHODS OF CONTROLLING FLOW OF BODILY FLUIDS

(75) Inventors: Chad Seaver, Knoxville, TN (US); Chris Arnott, Knoxville, TN (US); James Alexander Killeffer, Knoxville, TN (US)

(73) Assignee: Arkis, LLC, Knoxville, TN (US)

( * ) Notice: Subject to any disclaimer, the term of this patent is extended or adjusted under 35 U.S.C. 154(b) by 455 days.

(21) Appl. No.: 13/415,986

(22) Filed: Mar. 9, 2012

(65) Prior Publication Data

US 2012/0232461 A1    Sep. 13, 2012

Related U.S. Application Data

(60) Provisional application No. 61/451,894, filed on Mar. 11, 2011.

(51) Int. Cl.
| | | |
|---|---|---|
| *A61M 5/00* | (2006.01) | |
| *A61M 27/00* | (2006.01) | |
| *A61B 5/00* | (2006.01) | |
| *A61B 5/03* | (2006.01) | |

(52) U.S. Cl.
CPC ............ *A61M 27/006* (2013.01); *A61B 5/0017* (2013.01); *A61B 5/031* (2013.01); *A61M 27/002* (2013.01); *A61M 2205/3337* (2013.01)

(58) Field of Classification Search
CPC ............ A61M 27/002; A61M 27/006; A61M 2205/3337; A61B 5/0017; A61B 5/031
USPC ..................................................... 604/8, 9, 10
See application file for complete search history.

(56) References Cited

U.S. PATENT DOCUMENTS

| | | | | |
|---|---|---|---|---|
| 3,769,982 | A | | 11/1973 | Schulte |
| 4,560,375 | A | * | 12/1985 | Schulte et al. .................... 604/9 |
| 5,167,615 | A | * | 12/1992 | East et al. ......................... 604/9 |
| 5,387,188 | A | * | 2/1995 | Watson ............................. 604/8 |
| 5,643,195 | A | * | 7/1997 | Drevet et al. ..................... 604/9 |
| 6,193,682 | B1 | * | 2/2001 | Ahmed .............................. 604/9 |
| 6,383,160 | B1 | * | 5/2002 | Madsen .......................... 604/10 |
| 6,585,677 | B2 | | 7/2003 | Cowan, Jr. et al. |
| 6,926,691 | B2 | | 8/2005 | Miethke |
| 6,932,787 | B2 | | 8/2005 | Cowan et al. |
| 7,485,105 | B2 | * | 2/2009 | Wolf ................................. 604/9 |
| 2003/0139699 | A1 | * | 7/2003 | Rosenberg ....................... 604/9 |
| 2005/0010159 | A1 | * | 1/2005 | Reich et al. ...................... 604/8 |
| 2007/0032757 | A1 | * | 2/2007 | Medow et al. .................... 604/9 |
| 2009/0005720 | A1 | | 1/2009 | Ludin et al. |

* cited by examiner

*Primary Examiner* — Tatyana Zalukaeva
*Assistant Examiner* — Andrew J Mensh
(74) *Attorney, Agent, or Firm* — Pitts & Lake, P.C.

(57) ABSTRACT

Systems and methods to regulate flow of bodily fluids, such as cerebrospinal fluid (CSF), including a fluid chamber, an inlet port to receive the bodily fluid into the fluid chamber, an outlet port to remove the bodily fluid from the chamber, and a pressure element to regulate the amount of fluid flowing from the inlet port to the outlet port based on a pressure of the bodily fluid against an absolute pressure reference.

23 Claims, 6 Drawing Sheets

SYSTEMS AND METHODS OF CONTROLLING FLOW OF BODILY FLUIDS

CROSS-REFERENCE TO RELATED APPLICATIONS

This application claims priority from U.S. Provisional Application No. 61/451,894 filed on Mar. 11, 2011.

FIELD OF INVENTION

The present general inventive concept relates to systems and methods of treating hydrocephalus or the like, and more particularly, to an implantable, anti-siphoning cerebrospinal fluid (CSF) control system to monitor and drain excess CSF fluid, and methods of carrying out the same.

BACKGROUND

The human cranial vault contains the brain, blood vessels, and cerebrospinal fluid (CSF). The sutures of the cranium fuse by a year of age and the skull becomes a rigid structure. The architecture and physiology of the intracranial space allow for some compensation for additional intracranial volume such as hemorrhage, tumor, or excess CSF. When this compensatory capacity is exhausted, the contents act essentially as ideal fluids in a rigid container, making them subject to rapid rises in pressure when a relatively small volume of fluid is added. With sufficient rise in intracranial pressure (ICP), brain tissue is compressed and its blood supply is compromised resulting in brain damage and, if unchecked, death.

In the normal brain, CSF is secreted by tissue known as choroid plexus within cavities in the brain called ventricles. The CSF flows from the uppermost lateral ventricles through conduits into the more central third and then fourth ventricles, then flowing out of the brain to surround the spinal cord and brain. Ultimately, the CSF is absorbed on the outer surface of the brain by cells comprising the arachnoid villi. This is a continuous circulation, amounting to approximately 400 cc/day.

Any interruption in CSF circulation can result in excess CSF within the intracranial space, a condition known as hydrocephalus. In mild cases, CSF fills the ventricles excessively and stretches the cells of the brain resulting in neurological dysfunction. In severe cases, the rise in ICP is sufficient to result in brain damage and death.

The two general categories of hydrocephalus are communicating and non-communicating. Communicating hydrocephalus is caused by inability of the arachnoid villi to adequately absorb CSF. This can result from scarring due to previous hemorrhage or infection. A less-well understood form of this, known as normal pressure hydrocephalus (NPH), occurs in the elderly and is thought to be a derangement in the normal balance of CSF secretion and re-absorption. Non-communicating hydrocephalus is a consequence of mechanical obstruction of the normal flow of CSF, commonly by tumors or congenital or acquired narrowing of CSF conduits.

The most common contemporary treatment of hydrocephalus is to divert the flow of CSF. One strategy in obstructive hydrocephalus is to surgically pierce a hole in the bottom of the third ventricle, a third ventriculostomy, bypassing the obstruction. More commonly, CSF is diverted to a space in the body that has a large capacity to absorb it such as the peritoneum, pleura, or bloodstream. This strategy can be used with obstructive or communicating hydrocephalus and is accomplished by a device known as a shunt.

A shunt for CSF diversion typically consists of a synthetic tube placed through a hole drilled in the skull and passed through the brain into the ventricle. This is connected to a tube passed under the skin that terminates in the desired location. The shunt may be fitted with a valve designed to control pressure and flow as well as a device designed to mitigate over-drainage due to siphoning with upright posture.

Currently available shunt technology has several shortcomings. Valve technology is often inadequate to provide the optimal level of drainage. Under-drainage results in elevated ICP and over-drainage can result in headaches or hemorrhage due to collapse of the brain and tearing of surface blood vessels. Differential pressure based shunts, even with "anti-siphon countermeasures", often do not adapt well to changes in posture, to fluctuating CSF production and ICP, or to changes in intracranial CSF dynamics over time. Patients with shunts and persistent headaches frequently present a challenge because it is unclear whether there is subtle over- or under-drainage. The simple externally adjustable valves available currently force the clinician to guess at the appropriate pressure setting and accept that the system cannot adapt to fluctuations in demand.

Partial or complete obstruction of shunts is common and can be due to blockage by aggregated protein, blood, or tissue invasion into the conduit as well as mechanical disconnection of the shunt system. Shunt failure is often difficult to identify until intracranial compensatory mechanisms are depleted and there is a precipitous rise in ICP constituting a surgical emergency. Detection of early shunt malfunction usually requires clinical suspicion followed by invasive testing consisting of accessing the system through the skin with a needle, measuring the pressure with a manometer, and sometimes instilling radioactive or iodinated contrast medium for radiographic imaging. These procedures can be difficult to interpret and introduce the risk of infecting or damaging the shunt, both of which can carry significant morbidity and mortality for the patient.

SUMMARY

Embodiments of the present general inventive concept provide an adjustable, implantable, shunt system to regulate the flow of bodily fluids in a patient, such as cerebrospinal fluid (CSF).

Example embodiments include a master control unit, a continuously variable flow resistance assembly, an anti-siphoning valve, and an integrated Siamese-type drain tube to drain excess CSF fluid from the brain and communicate electrical control signals.

Additional features and embodiments of the present general inventive concept will be set forth in part in the description which follows and, in part, will be obvious from the description, or may be learned by practice of the present general inventive concept.

Example embodiments of the present general inventive concept can be achieved by providing a shunt system which obviates or mitigates the limitations of current shunt therapy. In some embodiments, a master control unit (MCU) can be configured as an implantable active device, with a power source, that is microprocessor controlled containing a programmable continuously variable flow resistance anti-siphoning valve to prevent over/under-drainage. The MCU can also contain various diagnostic features, which enable the physician, or the patient, to monitor and control operation of the system.

Example embodiments of the present general inventive concept can also be achieved by providing a control system to regulate fluid flow in a patient, including a fluid chamber having an inlet port to receive a bodily fluid and an outlet port to discharge the received bodily fluid, a pressure element to sense a first pressure of the bodily fluid in the fluid chamber, and to sense a second pressure opposing the first pressure, and a valve member to regulate the amount of fluid discharged from the outlet port based on a comparison of the first pressure to the second pressure.

The valve member can be normally closed to close the outlet port, and the pressure element can move the valve member to open the outlet port when the first pressure reaches a threshold relative to the second pressure regardless of a pressure difference between the inlet port and the outlet port. The movement can be electrically, mechanically, or thermodynamically driven.

The pressure element can include a substantially diaphragm shape, a piston shape, a bellow shape, or other shapes chosen with sound engineering judgment. The first pressure can correspond to volumetric changes of bodily fluid in the fluid chamber facing a first surface of the pressure element, and the second pressure can correspond to a back pressure facing a second surface of the pressure element opposite to the first surface.

The control system can include an adjustable member spaced apart from the pressure member to define a pressure chamber between the pressure element and the adjustable member. The pressure chamber can be sealed or vented. The adjustable member can be perforated to alleviate any undesirable pressure buildup that would resist adjustment of the adjustable member. The adjustable member can be selectively controllable with respect to the pressure element to selectively adjust the second pressure by changing a characteristic of the adjustable member. The characteristic can be one or more of a volume, pressure, temperature, resistance, impedance, reluctance, capacitance, or tension, corresponding to the adjustable member.

The adjustable member can include a compression member disposed between the adjustable member and the pressure element. A change in volume of the pressure chamber can correspond to a change of force of the compression member.

The pressure chamber can define a volume between the pressure element and the adjustable member, and the pressure element can move with respect to the adjustable member when the valve is opened and closed such that the volume is reduced when the valve is opened relative to when the valve is closed.

The regulation of the fluid can be based on a volumetric difference between the first and second members.

The control system can include a vent member to regulate pressure in the pressure chamber while the pressure element and/or adjustable member move with respect to one another.

The control system can include a position sensor to sense a position of the pressure element. The control system can also include a control unit to calculate a flow rate of fluid discharged from the outlet port based on the position of the pressure element.

The position sensor can sense a position of the adjustable member, and the control unit can calculate the second pressure based on the position the adjustable member.

The position sensor can sense a position of the pressure element to generate a control signal to open or close the valve.

The pressure element and/or the adjustable member can be variable reluctance sensors.

The pressure element and/or the adjustable member can be a variable impedance sensor or a mass flow sensor.

The fluid chamber and the adjustable member can be separated by a diaphragm.

Example embodiments of the present general inventive concept can also be achieved by providing a shunt control system to regulate flow of bodily fluid in a patient, including a first catheter to receive the bodily fluid from a predetermined region of the patient, a second catheter to direct the bodily fluid to a fluid compatible region of the patient away from the predetermined region, a connection path to communicate the CSF fluid from the first catheter to the second catheter, a valve assembly interposed between the first and second catheter to regulate a flow rate of the bodily fluid communicated by the connection path, the valve assembly including aa fluid chamber having an inlet port to receive the bodily fluid from the first catheter, and an outlet port to discharge the received bodily fluid to the connection path, a pressure element to sense a first pressure of the bodily fluid in the fluid chamber and a second pressure opposing the first pressure, a master control unit electrically connected to the connection path, and a valve member to regulate the amount of fluid discharged from the outlet port, under the control of the master control unit, based on a comparison of the first pressure to the second pressure.

The connection path can include a fluid drain path integrated with an electrical communication path to form a monolithic tube structure to deliver the bodily fluid and electrical control signals along the connection path, respectively.

The valve member can be normally closed to close the outlet port, and the pressure element can move the valve member to open the outlet port when the first pressure reaches a threshold relative to the second pressure regardless of a pressure difference between the inlet port and the outlet port.

Example embodiments of the present general inventive concept can also be achieved by providing a method of regulating fluid flow in a patient, including providing a fluid chamber having an inlet port to receive a bodily fluid and an outlet port to discharge the received bodily fluid, sensing a first pressure of the bodily fluid in the fluid chamber, sensing a second pressure of the pressure element opposing the first pressure, and opening and closing the outlet port based on a comparison of the first pressure to the second pressure.

Example embodiments of the present general inventive concept can also be achieved by providing an adjustable shunt control system to regulate flow of cerebrospinal fluid (CSF), including a fluid chamber having an inlet port to receive the CSF and an outlet port to remove the received CSF from the fluid chamber, a pressure element having a first surface to sense a fluid pressure of the bodily fluid in the fluid chamber, and second surface to sense a second pressure opposite to the first pressure, and a valve member connected between the inlet port and outlet port to open and close the outlet port based on a difference between the first and second pressure.

The shunt control system can include an environmental calibration unit to calibrate the pressure sensor. The environmental calibration unit can include a barometric pressure sensor externally or internally coupled to the master control unit to calibrate the sensor using atmospheric pressure external to the patient.

The environmental calibration unit can be wired or wireless. The environmental calibration unit can measure atmospheric pressure relative to the fluid discharge area and/or fluid chamber.

BRIEF DESCRIPTION OF THE DRAWINGS

The following embodiments are representative of example techniques and structures designed to carry out various objectives of the present general inventive concept, but those skilled in the art will appreciate that the present general inventive concept is not limited to these example embodiments, and that other techniques and structures could be chosen with sound engineering judgment to achieve the same or similar results as the example embodiments described herein. Moreover, in the accompanying drawings and illustrations, the sizes and relative sizes, shapes, and qualities of lines, entities, and regions may be exaggerated for clarity. A wide variety of additional embodiments will be more readily understood and appreciated through the following detailed description of the exemplary embodiments, with reference to the accompanying drawings in which.

DETAILED DESCRIPTION

Reference will now be made to example embodiments of the present general inventive concept, examples of which are illustrated in the accompanying drawings and illustrations. The example embodiments are described herein in order to explain the present general inventive concept by referring to the figures.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

With reference to the accompanying figures, there is illustrated and described an example CSF shunt system which can be adjustable with regard to flow rate and/or pressure in a non-invasive fashion. Example embodiments of the present general inventive concept can be used to continually adjust to changes in posture and intracranial pressure based on a feedback loop. Some embodiments provide a clinician with non-invasive systems and methods of determining data regarding flow and pressure, both current and historical. Components of the present general inventive concept can be unitized to decrease the odds of mechanical disconnection. In some embodiments, the CSF shunt system can include compact solid-state electronics with minimal power requirements. The components can be rechargeable via non-invasive technology and compatible with large magnetic fields such as magnetic resonance scanners. In some embodiments, components of the present general inventive concept can be surgically accessible in the event of mechanical failure, and can be reconfigured (e.g., lengthened) to accommodate a patient's growth. A subcutaneous port can be provided to access CSF, and techniques of the present general inventive concept can be used to monitor the function of a third ventriculostomy and to treat high ICP in the event of mechanical failure.

Figure 1:
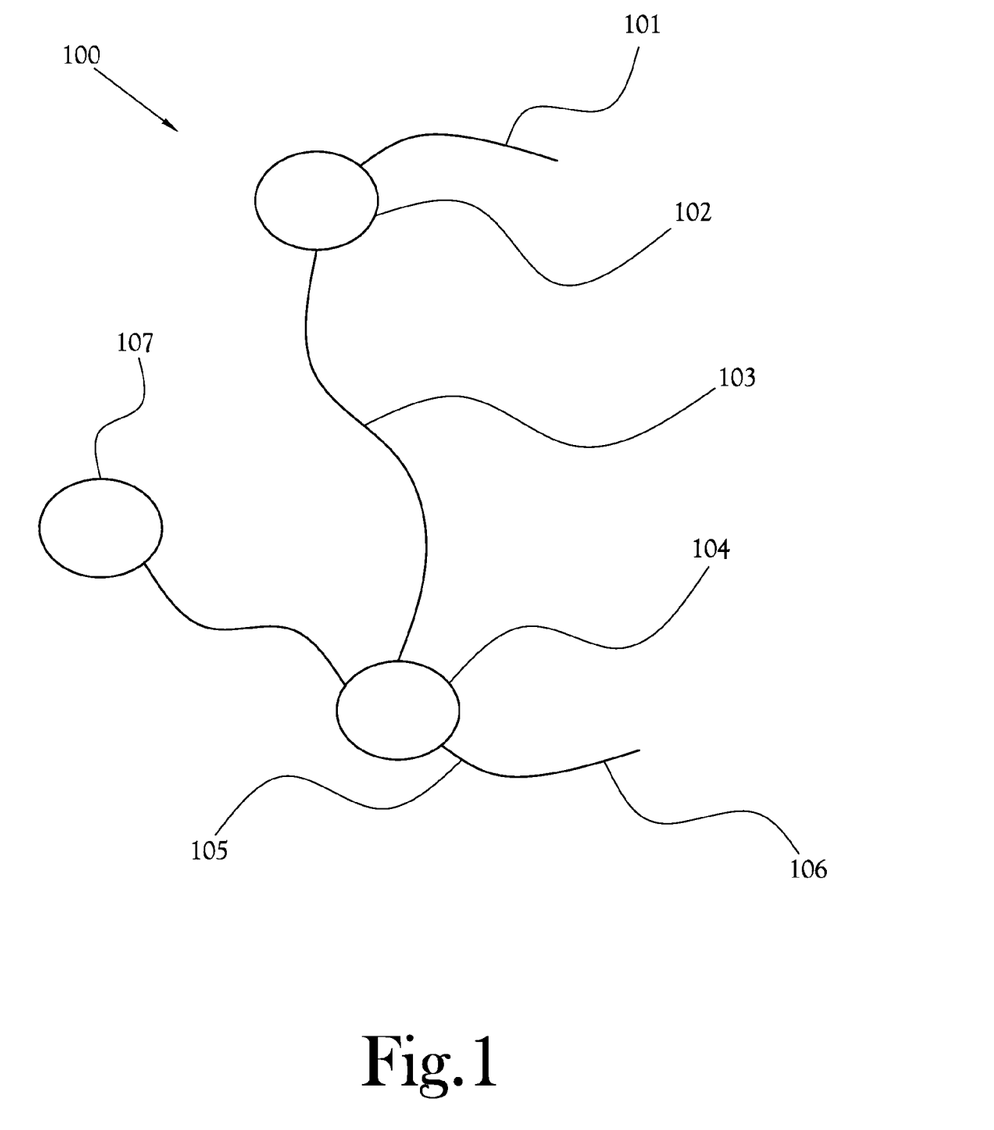
FIG. 1 is a schematic illustrating a CSF System configured in accordance with an example embodiment of the present general inventive concept.

Referring now to FIG. 1, a schematic representation of a Cerebrospinal Fluid (CSF) shunt system is indicated generally by 100. Shunt system 100 comprises a first catheter 101, a controllable valve, capable of continuous adjustment that substantially prevents siphoning, and sensor assembly 102, wherein the valve and sensor assembly may contain a syringe accessible self-sealing access port, and wherein the sensor assembly can be at least of one a position, acceleration, pressure or other sensor, a master control unit 104, a first connection path 103 between the valve and sensor assembly and the master control unit 104, a second catheter 106, a second connection path 105 between the master control unit and the CSF fluid destination. The first connection path can contain a CSF flow path and multiple communication paths within a monolithic (i.e. Siamese) tube, for communication between the master control unit and/or the valve and/or sensor assembly The CSF shunt system can be further sealed within a protective casing/membrane to protect the system from component disconnection, which can be caused by patient growth and/or scar tissue buildup. The protective casing may be monolithic with the Siamese tube thereby providing a integrated drain tube and sheath inclusive of the shunt valve. Having a smooth sealed system also helps to seal the system against bodily fluid intrusion as well as reducing the body's attachment to shunting components.

Master control unit 104 can be miniaturized and made of a biocompatible material, such as Titanium, such that it can be safely inserted and accepted in the patient's abdomen or other compatible locations, either intra-peritoneal or extraperitoneal, using a standard abdominal incision, and remain therein as needed to control and report CSF flow.

After master control unit 104 and valve sensor assembly 102 is inserted into the patient's abdomen and scalp, first connection path 103 can then be tunneled from the abdomen rostrally (or caudaly) to the scalp to serve as an drain path for excess CSF, which in an example embodiment is a ventricle, comprised of an integrated communications path and fluid transfer, to form the connection between 102 and 104. (As used herein, the term CSF space includes any space in the body that can generate an excess of CSF requiring drainage.) A small incision in the scalp can then be used to assist in the final positioning and connection of first catheter 101 within the patient's head in order to connect the first catheter 101 to the valve and sensor assembly 102 and then to 103. Similarly, second catheter 106 can be tunneled from below and connected to the master control unit 104 through the second connection path 105, up into the peritoneal cavity to serve as an outlet for the CSF. The tip of first and second catheter 101 and 106 is chosen to increase the flow of CSF drainage, and to reduce the likelihood of obstruction threat. The connection path 105 can be of a Siamese type to electrically connect to a pressure sensor at the end of catheter 106.

The shunt control system can include an environmental calibration unit 107, such as an external barometric pressure sensor, to measure the external environmental pressure to compensate and/or calibrate the shunt control system. For example, the calibration unit 107 can be connected, wired or wireless, to the master control unit 104, to measure the external atmospheric pressure to compensate for changes in external pressure to calibrate the pressure reference used to open and/or close the drainage valve 204 (FIG. 2).

Figure 2:
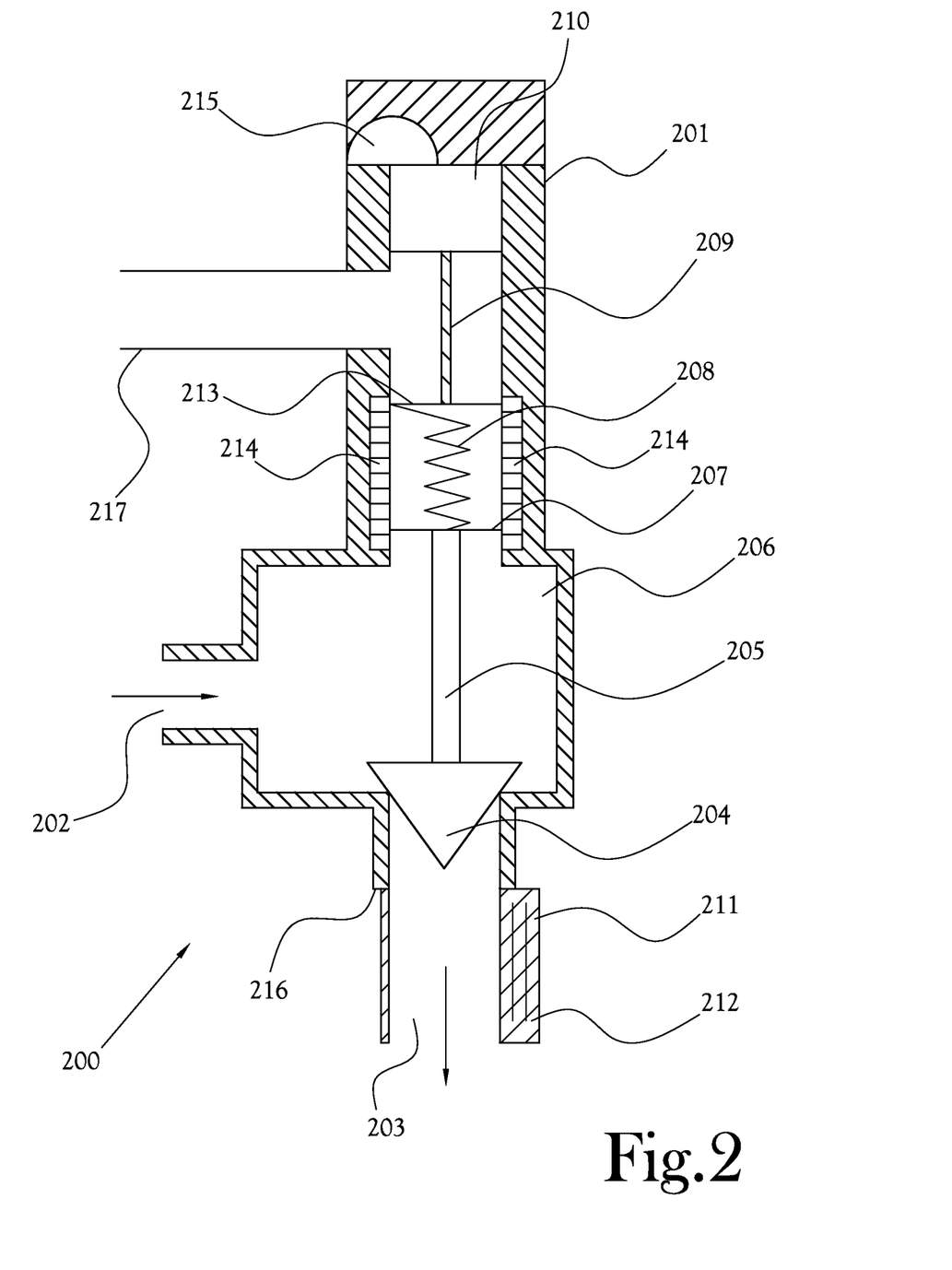
FIG. 2 is a schematic illustrating a valve and sensor assembly configured in accordance with an example embodiment of the present general inventive concept.

Referring now to FIG. 2, a schematic representation of an example Cerebrospinal Fluid (CSF) valve sensor assembly configured in accordance with an example embodiment of the present general inventive concept is indicated generally by 200. In the embodiment of FIG. 2, valve and sensor assembly 200 comprises a biocompatible housing 201, a CSF fluid inlet 202, a CSF fluid outlet 203, a valve 204, a pressure sensitive interface 207 (also referred to herein as pressure element 207), wherein the pressure element 207 can be substantially sealed against CSF or other bodily fluid intrusion, a connection 205 between the valve 204 and the pressure element 207, an adjustable compression element 208 (which may also be referred to as a tension or spring element) substantially providing for continuous adjustment, wherein the volume containing the adjustable pressure element is substantially sealed against CSF or other bodily fluid intrusion, an adjustable foundation base 213 (also referred to as adjustable member 213), wherein the adjustable foundation base 213 is substantially sealed against CSF or other bodily fluid intrusion, a positional translation device 210, a connection 209 between the adjustable foundation base 213 and the positional translation device 210, wherein the connection 209 transfers the position of the translation device 210 to the adjustable foundation base 213 which then adjusts the pressure exerted by the adjustable compression element 208 on the pressure sensitive interface 207, position sensing elements 214, wherein the position sensing elements 214 can detect the position of the pressure sensitive interface 207. The position can then be used to calculate CSF pressure and/or CSF flow rate. Geospacial sensor 215 can be used to sense a position of the patient, such as an orientation of the patient, to control operation of the positional translation device 210 and associated adjustable member 208 to adjust a force applied to the compression element 208. Outlet tubing connection 216 can be used to connect CSF outlet tubing 212, and integrated communication paths 211, wherein the communication paths are embedded in the CSF connection tubing 212 and can be substantially sealed against CSF or other bodily fluid intrusion, and wherein the opening of the valve sensor assembly 200 can be based on the absolute pressure difference between the CSF pressure and the pressure reference formed by the adjustable pressure reference comprised of 208, 209, and 210. For example, knowing the position of interface 207 can determine the size of the opening between the valve 204 and the outlet 203, allowing the control unit to calculate the flow rate of the bodily fluid. The sensing elements 214 can also track the position of the adjustable member 213 to determine pressure applied against the pressure sensitive interface 207. For example, if the adjustable compression element 208 is a spring, and the spring constant is known, the pressure can be derived based on the location of the foundation base 213 relative to the interface 207. In some embodiments, the sensing elements 214 can be light-based sensors to detect and measure a position of the pressure element 207 and adjustable member 213, although the present general inventive concept is not limited to any particular type of sensor. For example, Hall-effect or other electronic or electro-magnetic or electro-mechanical type position sensors could also be used in accordance with sound engineering judgment.

Using an non-differential pressure reading, such as absolute pressure difference allows for a built-in fail safe valve to drain the excess CSF based on the last set point of 210 by adjusting the resistance of 207 and 208 thereby setting the pressure translation device 210 and also prevents siphoning because the differential pressure across the valve has little effect on CSF fluid flow rate. For example, some embodiments can include a spring or other pressure method to enable the device to operate in the event the servo mechanism fails to modulate. Here, the spring 208 can be compressed or released based on the position of the adjustable member 213, which in turn is connected to a positional translation device 210 by connection 209 to reciprocally adjust the tension, or resistance, applied to the pressure sensitive interface 207. For example, a back pressure against the pressure sensitive interface 207 can be increased by downward movement of the adjustable member 213 to increase a force (e.g., tension) of compression element 208 since the pressure sensitive interface 207, connection 205, and valve 204 have limited downward movement due to valve closing. It is also possible to provide a positive stop to keep the pressure sensitive element 207 from further downward movement beyond a position for valve closing to prevent damage to the elements when pressure is increased by the adjustable members 208, 213 against the interface 207. Thus, the absolute pressure of the bodily fluid within the chamber 206 will control whether the valve 204 is open or closed, wherein the pressure required to open the valve 204 is variably controlled by the amount of pressure, or resistance, applied against the upward movement of the interface 207. Those skilled in the art will appreciate that a variety of other configurations in addition the configurations illustrated in the figures can be chosen with sound engineering judgment to achieve the same or similar results without departing from the scope and spirit of the present general inventive concept. In some embodiments the positional translation device 210 can be a stepper motor.

In operation, unwanted CSF siphoning can be mitigated since the absolute pressure of the fluid in chamber 206 controls valve 204 opening. Should siphoning occur, the fluid pressure in chamber 206 will drop and valve 204 will close. Thus, unwanted siphoning can be mitigated with an absolute pressure valve operation because the CSF flow is not based on the differential pressure drop across the valve. In other words, the valve 204 will remain closed regardless of the pressure difference between the inlet and outlet ports until the pressure in the fluid chamber 206 reaches a threshold value relative to the pressure reference opposing the interface, or pressure sensor, 207. A system and/or valve based on the absolute pressure comparison/reference allows for the management of intracranial pressure based on CSF pressure relative to a reference rather than the pressure difference across a valve as in the case of a ball check valve type. Thus, intracranial pressure regulation and CSF flow rate is substantially independent of patient position and pressure differences within the human body. Additionally, operating states of high parasitic differential pressure across the valve can act against the opening of the valve, such as but not limited to a low valve resistance setting in combination with an inclined patient position, or overcoming valve's parasitic opening resistance, the resistance of the valve could be compensated, temporarily during opening, to counteract regulation degradation caused by the differential pressure across the valve or the valve's opening resistance. This compensation can be created by measuring the differential pressure across the valve, with the pressure sensor and other sensors or additional pressure sensors and other sensors, and then temporarily adjusting the valves resistance opposite the parasitic differential pressure or parasitic opening resistance. Furthermore; the valve could be temporarily opened to overcome the parasitic effects. A vent 217 can be provided to the valve reference area where a variable volume exists. This could include a mechanism for utilizing the vent, including a directional valve, a fluid evacuate and gas charging mechanism based upon the servo operation during maintenance mode. The vent can connect to a dry volume to eliminate undesirable back pressure effects and to allow a fluid buffer in the case of fluid penetration into the pressure reference. For example, the vent 217 can release pressure buildup behind the adjustable element 213 and/or interface 207 when the valve 204 opens. In some embodiments, it is possible to make the back pressure between the element 208 and interface 207 due to translation of 207 negligible relative to the pressure contained by the vent 217 to ensure freer movement of the interface 207 relative to the element 208 during valve opening. Other embodiments can implement a pressure sensor in combination with a controller to sense the absolute pressure of the fluid within the chamber 206

Figure 3:
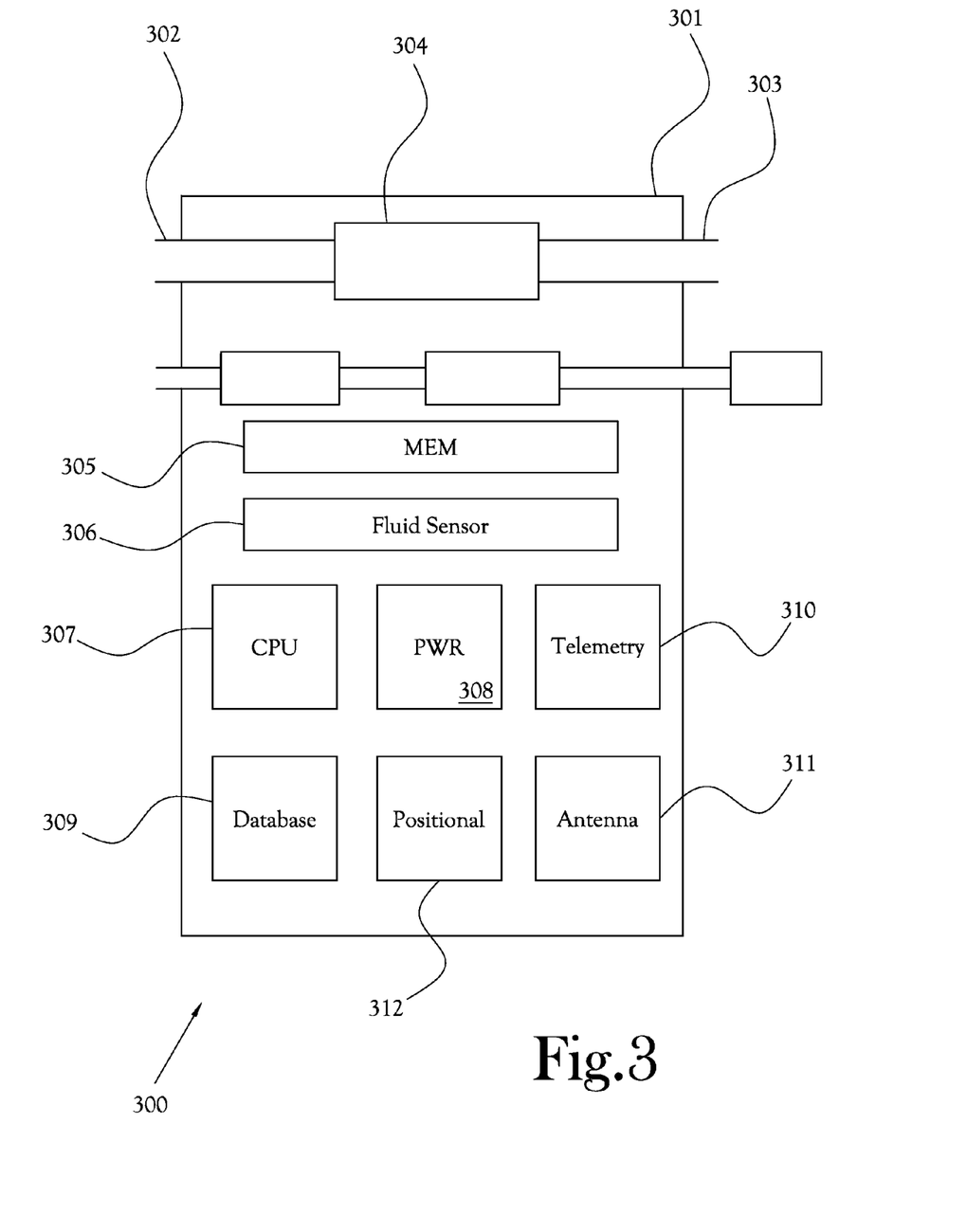
FIG. 3 is a schematic illustrating a Master Control Unit configured in accordance with an example embodiment of the present general inventive concept.

Referring now to FIG. 3, a schematic representation of a Cerebrospinal Fluid (CSF) master control unit is indicated generally by 300. Master Control Unit assembly 300 comprises a biocompatible housing 301, a CSF fluid inlet 302, wherein the CSF inlet 302 contains both a CSF fluid connection and/or communication connections, a CSF fluid outlet 303, an optional diagnostic unit 304 (for example, a pressure sensor), wherein the diagnostic unit is operable to measure properties of the CSF fluid, memory 305, optional fluid sensors 306, a central processing unit 307, power source 308, wherein the power source maybe a rechargeable battery charged with a wireless charger, a database 309, wherein the database contains wirelessly re-programmable operating software, a telemetry unit 310, wherein the telemetry unit allows bi-directional communication for uploading control information to the Master Control Unit 300 and/or downloading control and/or operating information from the Master Control Unit 300, antennae 311 capable of establishing communication with the Master Control Unit and wirelessly recharging the Master Control Unit battery, positional sensor 312. The Master Control Unit may also contain the valve and sensing unit 102 to form a single integrated CSF shunt Master Control Unit.

Figure 4:
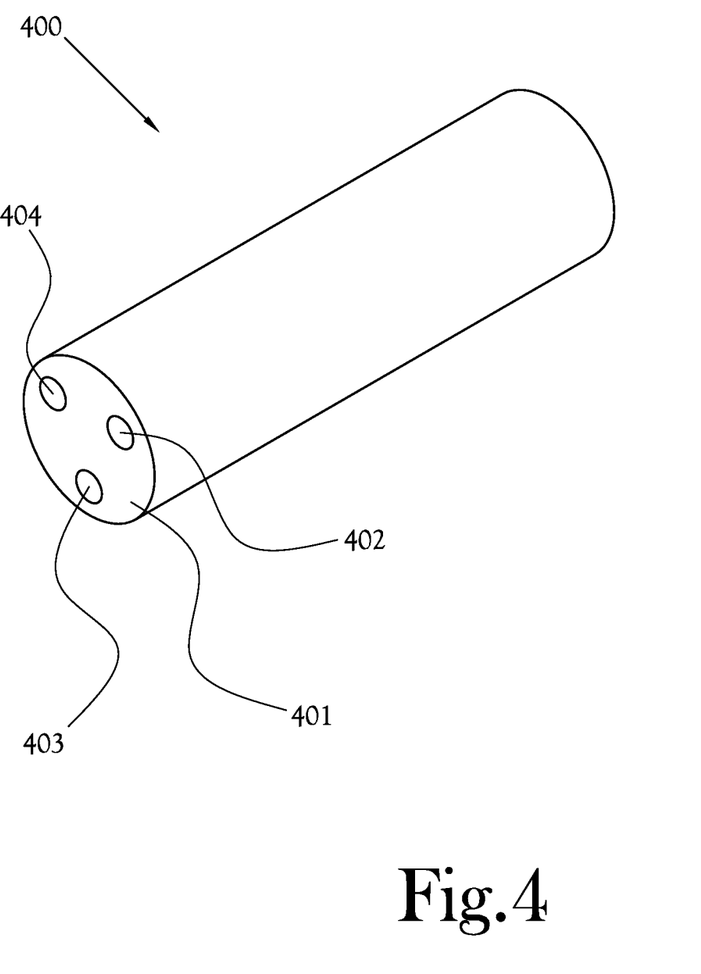
FIG. 4 is a schematic illustrating a CSF shunt and communication tube configured in accordance with an example embodiment of the present general inventive concept.

Referring now to FIG. 4, a schematic representation of an example Cerebrospinal Fluid (CSF) connection tube with a CSF flow path and multiple communication paths is indicated generally by 400. In the illustrated embodiment, the CSF tube assembly 400 comprises a Siamese tube constructed from a biocompatible material 401, such as silicone rubber, a CSF flow path 402, a first communication path 403, and a second communication path 404, wherein the communication paths 403 and 404 can be substantially sealed against CSF or other bodily fluid intrusion, and wherein the tube assembly may contain additional communication or flow paths. The tube assembly 400 can have more or less communication paths, depending on the desired number of electrical and/or fluid communication paths for a particular application. It is possible for the tube assembly 400 to include a removable stiffener as well. It is possible that a valve could be positioned inside the actual Siamese tube and reduce the likelihood of disconnection due to traditional barb/tie-off in which patient growth or scar tissue build-up applies pressure/tension and pulls the tube off the connection. Furthermore, the smooth outer jacket for the tube could reduce the likelihood of attachment by the human body as compared to a valve with more pronounced edges and adhesive surfaces. For example, a monolithic tube inclusive of the shunt valve could be provided in a case where the valve isn't within the controller.

Figure 5:
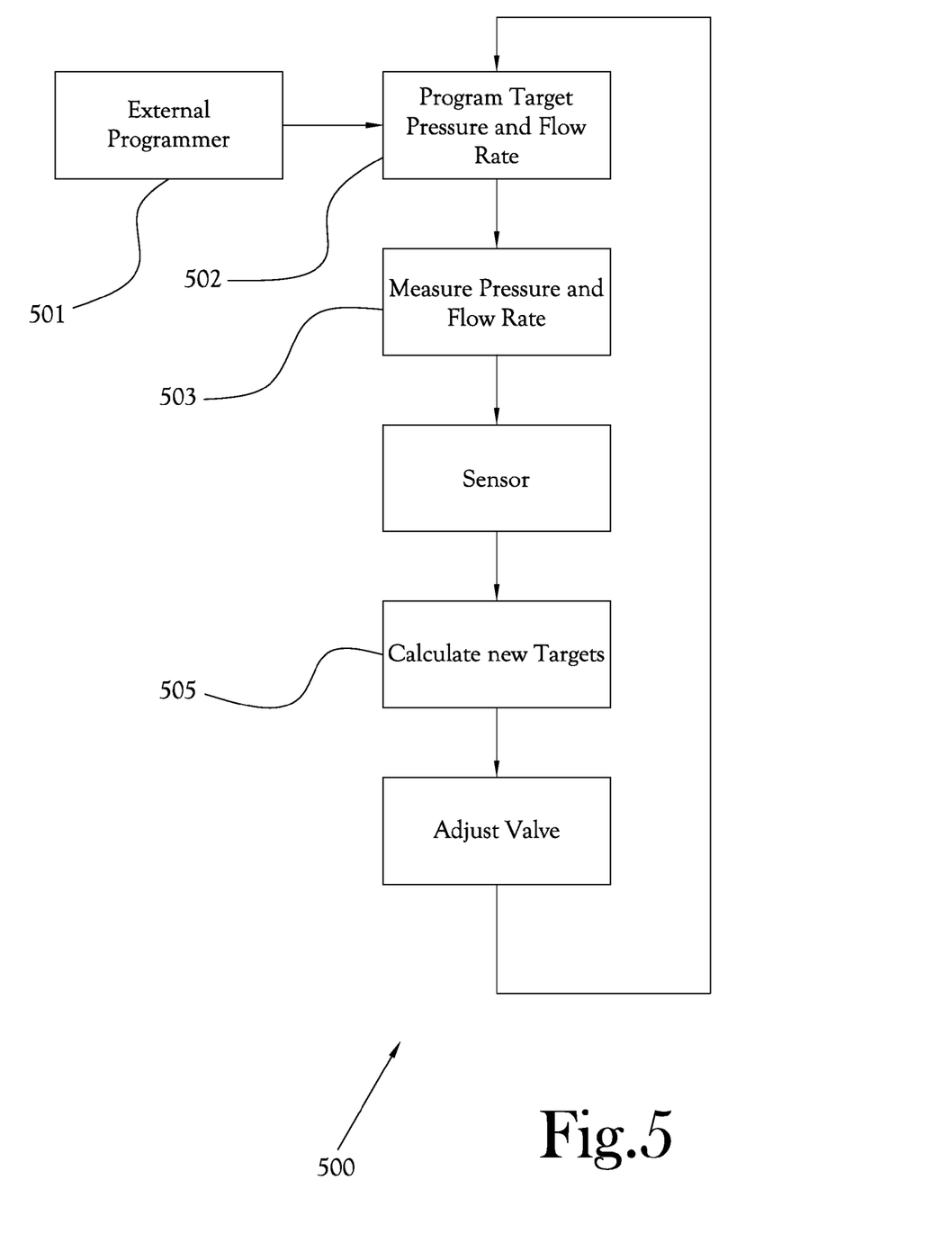
FIG. 5 is a flow chart illustrating CSF flow rate adjustment according to an example embodiment of the present general inventive concept.

Referring now to FIG. 5, a schematic representation of a Cerebrospinal Fluid (CSF) control program flow chart is indicated generally by 500. CSF control program chart 500 comprises an external programmer, 501, to remotely interface with the Master Control unit 300, wherein the external programmer communicates bidirectional with the Master Control Unit via RF signaling, and wherein the Master Control Unit operates independently after communication with the external programmer, a program target of CSF pressure and/or CSF flow rate 502 for various conditions, measurement or calculation of CSF pressure and/or flow rate 503, wherein the CSF pressure and flow rate are obtained from the valve and/or sensor assembly 200, measurement of acceleration, positional, environmental, or other sensor/s, wherein the sensor are located in the valve sensor assembly 200 and the Master Control Unit 300, calculation of a new pressure and/or flow rate target 505 based on the sensor inputs or calculation, adjust positional translation device, such as 210 or 607 and 609, based on the new pressure and/or flow rate targets, and then the process repeats. The new pressure target can be updated manually or automatically and based on user control, elapsed time, or substantially continuously. An optional environmental calibration unit 107 can be used to measure external environmental pressure and/or a sensor can be provided separately or integrated with 107 to measure the discharge area's pressure.

Figure 6:
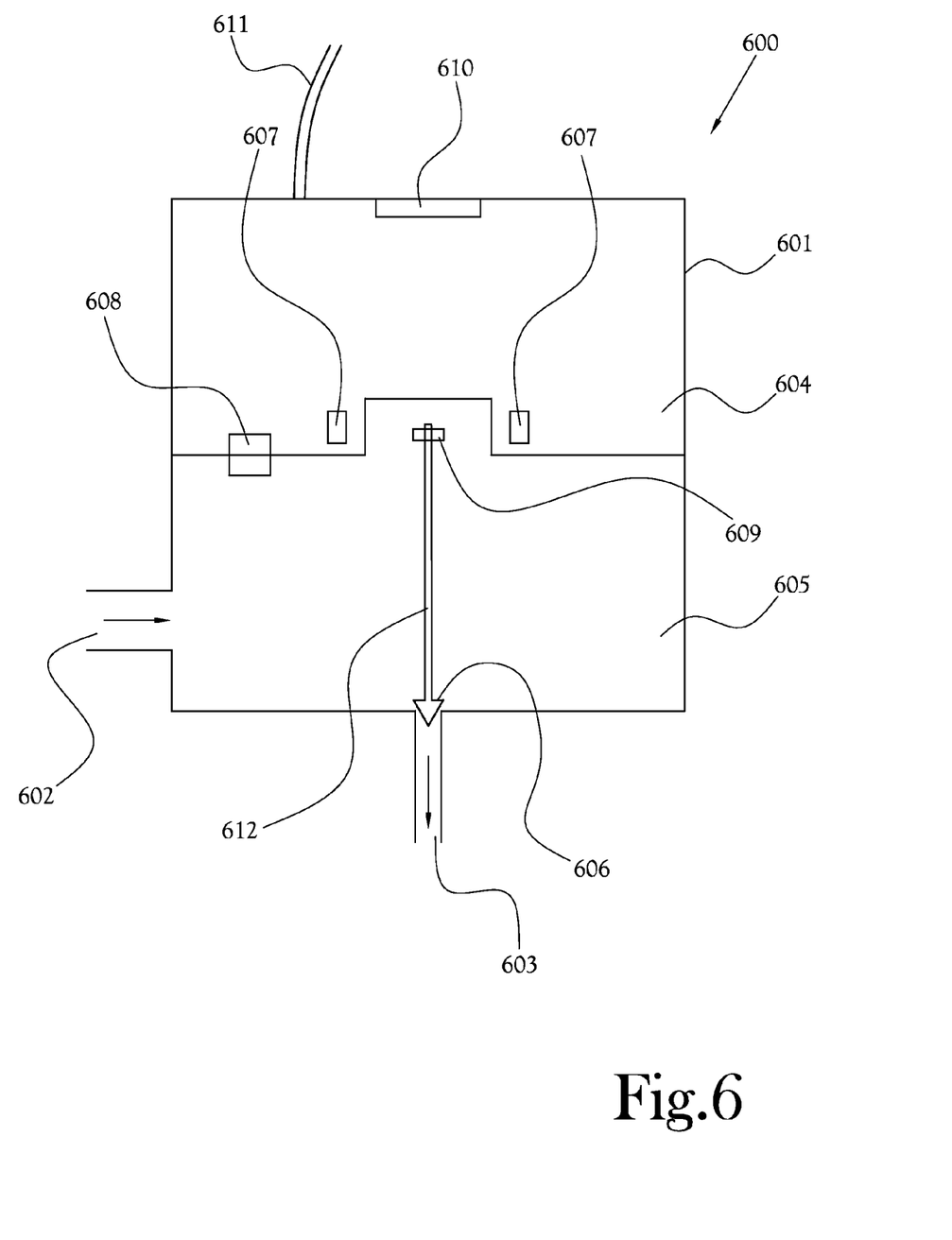
FIG. 6 is a diagram illustrating a valve and sensor assembly configured in accordance with another example embodiment of the present general inventive concept.

Referring now to FIG. 6, a schematic representation of an alternative Cerebrospinal Fluid (CSF) valve sensor assembly is indicated generally by 600. According to this example embodiment, valve and sensor assembly 600 comprises a biocompatible housing 601, a CSF fluid inlet 602, a CSF fluid outlet 603, a valve 606, a CSF fluid pressure chamber 605, a absolute pressure chamber 604, wherein the CSF fluid pressure chamber 605 and absolute pressure reference chambers 604 can be substantially sealed to separate the fluid pressure and reference pressure chambers, a connection 612 between the valve 606, a first communication device attached to the connection 612 substantially providing for continuous adjustment of the opening and closing of the valve 606 by a coupled communication, a second communicating device 607 coupled to the first communication device 609, wherein the coupling between the communicating devices controls the opening and closing of valve 606, a pressure sensor 608, wherein pressure sensor 608 can be an absolute and/or sealed pressure sensor that measures the pressure difference between pressure chambers 604 and 605, an optional geospacial sensor 610, a communication link 611 between the valve assembly 601 and a control unit. In some embodiments the pressure sensor 608 can be a variable reluctance pressure sensor, or other type of pressure sensor, for example, an impedance or strain-based transducer, and the geospacial sensor 610 can be a gravitational and/or accelerometer sensor. The pressure sensor 608 can include an adjustment device, such as a heater element, to apply heat to the pressure 608, enabling the pressure reference to be adjusted thermodynamically. However, the present general inventive concept is not limited to a heater coil or other heating device, and it is understood that a variety of other electrical, thermal, and/or mechanical devices could be implemented to selectively adjust the pressure reference of the pressure sensor without departing from the broader scope and spirit of the present general inventive concept. In some embodiments, the pressure sensor can generate a signal based on a changed capacitance of the sensor caused by a pressure change in the pressure chamber 605 moving an interfacial surface of the sensor.

The present general inventive concept can be embodied as computer-readable codes on a computer-readable medium. The computer-readable medium can include a computer-readable recording medium and a computer-readable transmission medium. The computer-readable recording medium can be any data storage device to store data as a program or instructions which can be thereafter read by a computer system. Examples of the computer-readable recording medium include read-only memory (ROM), random-access memory (RAM), CD-ROMs, DVDs, magnetic tapes, floppy disks, and optical data storage devices. The computer-readable recording medium can also be distributed over network coupled computer systems so that the computer-readable code is stored and executed in a distributed fashion. The computer-readable transmission medium can transmit carrier waves or signals (e.g., wired or wireless data transmission through the Internet). Also, functional programs, codes, and code segments to accomplish the present general inventive concept can be easily construed by programmers skilled in the art to which the present general inventive concept pertains.

It is noted that the simplified diagrams and drawings do not illustrate all the various connections and assemblies of the various components, however, those skilled in the art will understand how to implement such connections and assemblies, based on the illustrated components, figures, and descriptions provided herein.

While the present general inventive concept has been illustrated by description of example embodiments and while the illustrative embodiments have been described by referring to the drawings, it is not the intention of the applicant to restrict or in any way limit the scope of the appended claims to the illustrative examples. It is noted that numerous variations, modifications, and additional embodiments are possible, and accordingly, all such variations, modifications, and embodiments are to be regarded as being within the spirit and scope of the present general inventive concept. For example, the shunt valve may be located in various positions of the human body, and could be integrated or separated from the controller itself, or within the controller. Those skilled in the art will appreciate that the exact mechanism for the absolute pressure reference as well as the valve position and pressure readings may be configured in various ways. For example, an actual pressure sensor may be provided in the valve body. Furthermore, although embodiments of the present general inventive concept have been described in connection with treatment of conditions such as hydrocephalus, embodiments of the present general inventive concept also find application in treatment of a variety of other conditions in other parts of the body, such as the lungs, liver, bladder, to drain excess fluid therefrom.

Furthermore the concepts taught by the invention can be applied to the treatment of other diseases including but not limited to pleural effusion due to infectious process, neoplazm, etc, liver cirrhosis with ascites, and/or any other diseases where the treatment involves the removal/transfer of excess fluid from a first biological area to a second biological area. In the case of liver cirrhosis with ascites, fluid could be shunted away, in a controlled manner, from the abdominal cavity, the first biological area, to a second biological area such as the bladder or intestine. In the case of pleural effusion, fluid could be shunted away, in a controlled manner, from the pleural cavity, the first biological area, to a second biological area such as the peritoneal cavity.

Such embodiments are intended to be within the broader scope and spirit of the present general inventive concept. Thus, the present general inventive concept in its broader aspects is therefore not limited to the specific details, representative apparatus and methods, and illustrative examples illustrated and described. Accordingly, departures may be made from such details without departing from the spirit or scope of applicant's general inventive concept It is also noted that numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Accordingly, while the present general inventive concept has been illustrated by description of several example embodiments, it is not the intention of the applicant to restrict or in any way limit the scope of the inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings.

What is claimed is:

1. A control system to regulate fluid flow in a patient, comprising:
    a fluid chamber having an inlet port to receive a bodily fluid and an outlet port to discharge the received bodily fluid;
    a pressure chamber separated and substantially sealed from the fluid chamber;
    a pressure element configured to sense a first pressure of the bodily fluid in the fluid chamber, and to sense a second pressure of the pressure chamber opposing the first pressure,
    wherein the pressure chamber is configured such that the second pressure is an absolute pressure reference independent of pressure differences within the patient's body; and
    a valve member to regulate the amount of fluid discharged from the outlet port based on a comparison of the first pressure to the absolute pressure reference,
    wherein the pressure chamber includes a vent connected to a dry volume to reduce back pressure effects on the absolute pressure reference when the valve member opens the outlet port.

2. The control system of claim 1, wherein the valve member is normally closed to close the outlet port, and wherein the pressure element causes the valve member to open the outlet port when the first pressure reaches a threshold relative to the second pressure regardless of a pressure difference between the inlet port and the outlet port.

3. The control system of claim 1, wherein the first pressure corresponds to volumetric changes of bodily fluid in the fluid chamber facing a first surface of the pressure element, and the second pressure corresponds to a back pressure facing a second surface of the pressure element opposite to the first surface.

4. The control system of claim 3, wherein the control system comprises an adjustable member to adjust a pressure reference of the pressure element, the adjustable member being selectively controllable with respect to the pressure element to selectively adjust the second pressure by changing a characteristic of the adjustable member.

5. The control system of claim 4, wherein the adjustable member includes a compression member disposed between the adjustable member and the pressure element, and the change in characteristic corresponds to a change in compression of the compression member.

6. The control system of claim 4, wherein the adjustable member is spaced apart from the pressure element to define a pressure chamber having a volume between the pressure element and the adjustable member, and the pressure element moves with respect to the adjustable member when the valve is opened and closed such that the volume of the pressure chamber is changed when the valve is opened relative to when the valve is closed.

7. The control system of claim 4, wherein the characteristic is adjusted by one or more of heat, control signal, and compression.

8. The control system of claim 6, further comprising a vent member to ventilate pressure of the pressure chamber when the valve is opened and/or closed.

9. The control system of claim 6, further comprising a position sensor to sense a position of the pressure element, and a control unit to calculate a pressure and/or flow rate of fluid discharged from the outlet port based on the position of the pressure element.

10. The control system of claim 9, wherein the position sensor senses a position and/or temperature of the adjustable member, and the control unit calculates the second pressure based on the position and/or temperature of the adjustable member.

11. The control system of claim 4, further comprising a position sensor to sense a position of the adjustable member and/or pressure element to generate a control signal to open or close the valve.

12. The control system of claim 4, wherein the second pressure is a substantially vacuum pressure opposing the first pressure.

13. The control system of claim 1, further comprising a calibration unit to calibrate the comparison between the first and second pressure based on an external environmental pressure.

14. The control system of claim 4, wherein the fluid chamber and the adjustable member are separated by one or more of a diaphragm, a piston, and a bellows.

15. A shunt control system to regulate flow of bodily fluid in a patient, comprising:
   a first catheter to receive the bodily fluid from a predetermined region of the patient;
   a second catheter to direct the bodily fluid to a fluid compatible region of the patient away from the predetermined region;
   a connection path to communicate the bodily fluid from the first catheter to the second catheter;
   a valve assembly interposed between the first and second catheter to regulate a flow rate and/or pressure of the bodily fluid communicated by the connection path, the valve assembly comprising:
      a fluid chamber having an inlet port to receive the bodily fluid from the first catheter, and an outlet port to discharge the received bodily fluid to the connection path;
      a pressure chamber separated and substantially sealed from the fluid chamber;
      a pressure element configured to sense a first pressure of the bodily fluid in the fluid chamber, and to sense a second pressure of the pressure chamber opposing the first pressure,
      wherein the pressure chamber is configured such that the second pressure is an absolute pressure reference independent of pressure differences within the patient's body;
      a master control unit coupled to the connection path; and
      a valve member to regulate the amount of fluid discharged from the outlet port, under the control of the master control unit, based on a comparison of the first pressure to the absolute pressure reference,
      wherein the pressure chamber includes a vent connected to a dry volume to reduce back pressure effects on the absolute pressure reference when the valve member opens the outlet port.

16. The shunt control system of claim 15, wherein the connection path comprises a fluid drain path integrated with an electrical communication path to form a monolithic tube structure to deliver the bodily fluid and electrical and/or mechanical control signals along the connection path, respectively.

17. The control system of claim 15, wherein the valve member is normally closed to close the outlet port, and wherein the pressure element causes the valve member to open the outlet port when the first pressure reaches a threshold relative to the second pressure regardless of a pressure difference between the inlet port and the outlet port.

18. A method of regulating fluid flow in a patient, comprising:
   providing a fluid chamber having an inlet port to receive a bodily fluid and an outlet port to discharge the received bodily fluid;
   providing a pressure chamber separated and substantially sealed from the fluid chamber;
   providing a pressure element to sense a first pressure of the bodily fluid in the fluid chamber and to sense a second pressure of the pressure chamber opposing the first pressure, the second pressure defining an absolute pressure reference independent of pressure differences within the patient's body; and
   connecting the pressure element to a valve member such that the pressure element moves the valve member to open and close the outlet port based on a comparison of the first pressure to the absolute pressure reference,
   wherein the pressure chamber includes a vent connected to a dry volume to reduce back pressure effects on the absolute pressure reference when the valve member is opened or closed.

19. The method of claim 18, further comprising:
   opening the outlet port when the first pressure reaches a threshold relative to the second pressure regardless of a pressure difference between the inlet port and the outlet port.

20. A shunt control system to regulate flow of cerebrospinal fluid (CSF) in a patient, comprising:
   a fluid chamber having an inlet port to receive the CSF and an outlet port to remove the received CSF from the fluid chamber;
   a pressure chamber separated and substantially sealed from the fluid chamber;
   a pressure element configured to sense a first pressure of the CSF in the fluid chamber, and to sense a second pressure of the pressure chamber opposing the first pressure,
   wherein the pressure chamber is configured such that the second pressure defines an absolute pressure reference independent of pressure differences within the patient's body; and
   a valve member connected to the pressure element to move the valve member to open and close the outlet port based on a comparison between the first pressure and the absolute pressure reference,
   wherein the pressure chamber includes a vent connected to a dry volume to reduce back pressure effects on the absolute pressure reference when the valve member is opened or closed.

21. A control system to regulate fluid flow in a patient, comprising:
   a fluid chamber having an inlet port to receive a bodily fluid and an outlet port to discharge the received bodily fluid;

a pressure chamber separated and substantially sealed from the fluid chamber;

a pressure element to sense a first pressure of the bodily fluid in the fluid chamber, and to sense a second pressure of the pressure chamber opposing the first pressure, wherein the pressure chamber is configured such that the second pressure defines an absolute pressure reference independent of pressure differences within the patient's body; and a valve member connected to the pressure element such that movement of the pressure element moves the valve member to regulate the amount of fluid discharged from the outlet port based on a comparison of the first pressure to the absolute pressure reference, wherein the pressure chamber includes a vent connected to a dry volume to reduce back pressure effects on the absolute pressure reference when the pressure element moves the valve member.

22. The system of claim 21, wherein the movement of the pressure element and valve member is limited due to the valve member closing the outlet port.

23. The system of claim 21, wherein the valve member is spaced apart from the pressure element by a connecting member.

* * * * *